United States Patent [19]

Szalay et al.

[11] Patent Number: 4,778,759
[45] Date of Patent: Oct. 18, 1988

[54] GENETIC ENGINEERING IN CYANOBACTERIA

[75] Inventors: Aladar A. Szalay; John G. K. Williams, both of Ithaca, N.Y.

[73] Assignee: Boyce, Thompson Institute for Plant Research, Inc., Ithaca, N.Y.

[21] Appl. No.: 689,514

[22] Filed: Jan. 9, 1985

Related U.S. Application Data

[62] Division of Ser. No. 396,595, Jul. 9, 1982, abandoned.

[51] Int. Cl.$^4$ .................. C12N 15/00; C12N 1/20; C12N 1/00
[52] U.S. Cl. ................. 435/172.3; 435/253; 435/320; 935/29; 935/38; 935/6
[58] Field of Search ............. 435/172.3, 253, 317, 435/320; 935/29, 38

[56] References Cited

U.S. PATENT DOCUMENTS

| | | |
|---|---|---|
| 3,813,316 | 5/1974 | Chakrabarty . |
| 4,237,224 | 12/1980 | Cohen et al. . |
| 4,259,444 | 3/1981 | Chakrabarty . |
| 4,273,875 | 6/1981 | Manis . |
| 4,338,397 | 7/1982 | Gilbert et al. . |
| 4,338,400 | 7/1982 | Manis et al. . |
| 4,340,674 | 7/1982 | Manis et al. . |
| 4,342,832 | 8/1982 | Goeddel et al. . |
| 4,464,472 | 8/1984 | Carbon et al. ............ 435/255 |

FOREIGN PATENT DOCUMENTS

| | | |
|---|---|---|
| 0074808 | 3/1983 | European Pat. Off. . |
| 0127328 | 12/1984 | European Pat. Off. . |

OTHER PUBLICATIONS

Dubnau, The Molecular Biology of the Bacilli, vol. I, Academic Press, New York, pp. 147-178 (1982).
Harris-Warwick et al., J. Bacteriology, vol. 133, pp. 1246-1253 (1978).
Duncan et al., P NAS USA, vol. 75, pp. 3664-3668 (1978).
Contente et al., Plasmid, vol. 2, pp. 555-571, 1979.
van den Hondel et al., PNAS USA, vol. 77, pp. 1570-1574 (1980).
Sherman et al., J. Bacteriol., vol. 150, pp. 410-413 (1982).
Kuhlemeier et al., Mol. Gen. Genet., vol. 184, pp. 249-254.
Setlow et al., Recombinant DNA edited by Walton, Elsevier Scientific Pub. Co., pp. 83-91 (1981).
L. E. Post et al., CELL, vol. 25, Jul. 1981, pp. 227-232, MIT.
S. V. Shestakov et al., Biological Abstracts, vol. 75, No. 12, 1983, Abstract No. 90804, Biosciences Information Service, Philadelphia, PA.
Genetika 18(8): 1271-1275, 1982 *Abstract*.
Stassi et al., (1981) Proc. Natl. Acad. Sci USA 78: 7028-7032.
Claverys et al., (1980) Proc. Natl. Acad. Sci. USA 77: 3534-3538.
Iglesias et al. (1981) Mol. Gen. Genet. 184: 405-409.
Ruvkun et al. (1981) Nature 289: 85-88.
Canosi et al. (1978) Mol. Gen. Genet. 166: 259-267.
Gryczan et al. (1980) Mol. Gen. Genet. 177: 459-467.
de Vos et al. (1981) Mol. Gen. Genet. 181: 424-433.
Canosi et al. (1981) Mol. Gen. Genet. 181: 434-440.

Primary Examiner—Alvin E. Tanenholtz
Attorney, Agent, or Firm—Banner, Birch, McKie & Beckett

[57] ABSTRACT

A procaryotic microorganism and a method for its production is provided wherein the microorganism contains at least one stable foreign DNA portion in the chromosome. The disclosed microorganisms and their progeny are substantially free of genetic rearrangement involving the foreign DNA. In a preferred embodiment, cyanobacteria are employed. The microorganisms are produced by introducing into the cell an insertion vehicle that contains foreign DNA ligated between two portions of DNA homologous to adjacent portions of the recipient's chromosome.

20 Claims, 1 Drawing Sheet

GENETIC ENGINEERING IN CYANOBACTERIA

This application is a division of application Ser. No. 396,595, filed July 9, 1982 and now abandoned.

TECHNICAL FIELD

The present invention relates to procaryotic organisms that have foreign DNA stably inserted in a chromosome and a method for their production.

BACKGROUND OF THE INVENTION

Practical methods for introducing foreign DNA into bacteria and other organisms are, of course, known in the art. These methods employ recombinant DNA technology to construct chimeric plasmid DNA molecules which contain pieces of foreign DNA. The chimeric plasmids are designed to replicate autonomously as an extrachromosomal DNA species in a procaryotic host such as *E. coli*. In yeast, the chimeric plasmid may either replicate extrachromosomally or it may integrate into yeast chromosomes, although such integration tends to be unstable. When employing such genetically engineered microorganisms to manufacture products, it is important to continously select for the presence of the foreign DNA in the recipient organism because the foreign DNA carried on a plasmid or in integrated form tends to be unstable and can be lost in daughter cells.

Many applications of genetic engineering technology are centered around the production of proteins via genetically altered microorganisms (e.g., insulin or interferon). Production of a protein often requires only that a single gene encoding the specific protein be introduced into the recipient organism. The synthesis of more complex metobolic products, however, may require the introduction of several foreign DNA segments or genes to create new biochemical pathways. For example, the production of nonprotein products could be achieved if genes encoding the production of enzymes which operate on nonprotein substrates to produce the desired product could be stably introduced into a microorganism. It is difficult to maintain a multistep biochemical pathway using "traditional" technology because of the instability of the foreign DNA introduced via the chimeric plasmid DNA molecules. Simply too many genes must be introduced and maintained collectively in the recipient organism. A means for introducing several foreign DNA segments or genes stably in a recipient organism would, therefore, be a valuable contribution to the art.

SUMMARY OF THE INVENTION

It is an object of the present invention to provide procaryotic microorganisms which have at least one foreign DNA portion stably inserted into the chromosome.

Another object of the present invention is to provide a unicellular photosynthetic microorganism which contains at least one stable foreign DNA portion in a chromosome.

It is a further object of the present invention to provide a method for stably inserting a foreign gene in a chromosome of a unicellular microorganism.

It is also an object of the present invention to provide a method of producing chemicals, including chemicals other than proteins, employing microorganisms.

One aspect of the present invention is directed to a procaryotic microorganism containing at least one stable foreign DNA portion covalently bonded directly to chromosomal DNA wherein said microorganism and its progeny are substantially free of genetic rearrangements involving said foreign DNA. These microorganisms, which may be made by a process of the present invention, can contain multiple foreign DNA portions or genes stably incorporated into the chromosomal genome. It is possible to stably encode complete biochemical pathways foreign to a microorganism into the chromosome so that useful chemicals, particularly chemicals other than proteins, can be made in vivo by a practical method. In a preferred embodiment of the present invention the microorganism is a cyanobacterium. This allows useful products to be made photosynthetically. The present invention also encompasses pure cultures of the above microorganisms which do not have to be subjected to constant selective pressure in contrast to microorganisms containing foreign genes inserted into plasmids.

Another aspect of the present invention provides a method of producing a microorganism having at least one stable foreign DNA portion in its chromosome, said method comprising: (a) providing a DNA insertion vehicle containing first ad second DNA portions containing DNA homologous to adjacent portions of a chromosome in said microorganism, said homologous DNA in said first and second DNA portions oriented in relation to each other in the same manner as said homologous chromosomal DNA portions in said microorganism; and a third DNA portion containing DNA foreign to said microorganism, said third DNA portion located between and covalently bonded to said first and second DNA portions; and (b) introducing said DNA insertion vehicle inside the cell membrane of said microorganism to effect incorporation of the genetic material of said foreign DNA into the chromosomal genome of said microorganisms.

In one preferred aspect, the present invention contemplates a circular DNA insertion vehicle which facilitates the stable insertion of foreign DNA into the chromosome of a procaryotic microorganism, said circular DNA insertion vehicle comprising: (a) a first DNA segment comprising first and second DNA portions containing DNA homologous to adjacent portions of a chromosome in a microorganism, said first and second DNA portions oriented in relation to each other in the same manner as said homologous chromosomal DNA portions in said microorganism; and a third DNA portion containing DNA foreign to said microorganism that expresses a selectable phenotype located between and covalently bonded to said first and second DNA portions, and a single restriction site in said first DNA segment for a particular restriction enzyme at a location nonessential to said expressable phenotype between said first and second DNA portions; and (b) a second DNA segment containing a DNA portion that is not homologous to the chromosomal DNA in said microorganism.

The various aspects of the present invention will be apparent to those skilled in the art from the following description.

DETAILED DESCRIPTION OF THE INVENTION

Figure 1:
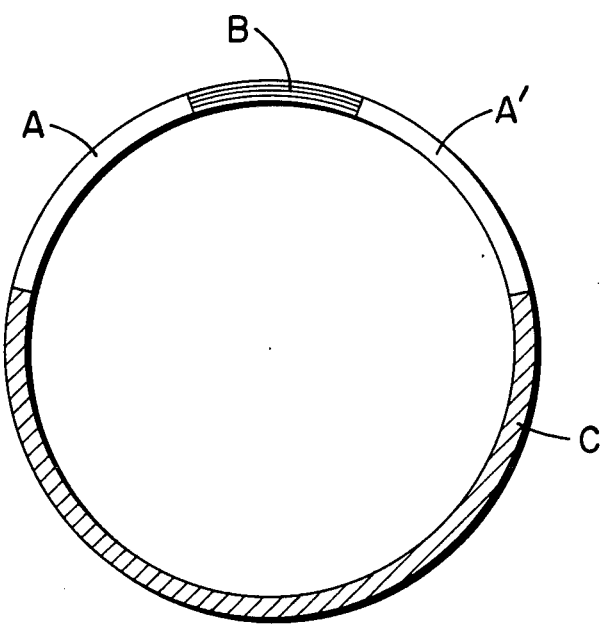
FIG. 1 is a schematic representation of the preferred circular chimeric DNA insertion vehicle of the present invention in its simplest form.

The present invention is directed to procaryotic microorganisms which have at least one foreign DNA portion stably inserted in the chromosomes. Genetically engineered microorganisms of the prior art generally contain foreign genes either in plasmids or unstably integrated, as in yeast, into the chromosomes. Plasmids can be lost upon reproduction in some daughter cells and unstable foreign genes integrated into chromosomes are subject to deletion. In contrast, the foreign DNA in the microorganisms of the present invention is ligated (i.e., covalently bonded) directly to the chromosomal DNA of the microorganism, not to plasmid DNA or other DNA such as viral DNA or transposable elements. Typically, the foreign DNA in the present invention is contained within nonessential DNA in the chromosome.

A DNA segment or portion is a linear length of DNA. A DNA segment as used herein is a longer length of DNA than a DNA portion.

Foreign DNA, as used herein, includes synthetic DNA that does not exist in nature, chromosomal or plasmid DNA that is derived from a genus other than the recipient organism's genus, or a viral DNA length that does not have the ability to naturally infect or transfect the recipient organism. Excluded from foreign DNA, however, is a DNA length that is a transposable element (e.g., transposon or insertion sequence) in the recipient organism. A transposable element is a length of DNA that interacts with a second DNA molecule (e.g., chromosome of the recipient) by site-specific recombination to produce new linkage relationships in the second DNA molecule, including inversion or deletion of DNA in the second DNA molecule, or addition of the transposable element to the second DNA molecule. See C. M. Radding, (1978) *Am. Rev. Biochem.* 47: 847-880; *DNA Insertion Elements, Plasmids & Episomes* (A. Bukhari, J. Shapiro & S. Adhya eds., Cold Spring Harbor Labratory 1977). DNA "derived from a genus other than the recipient organism's genus" is DNA found in nature only in organisms of other genera. Even if the particular copy of DNA employed in the present invention was not immediately derived from another genus, the DNA is still "derived from" another genus if it is found in nature only in a genus or genera other than the genus of the recipient organism.

Viral DNA that can infect or transfect a recipient is excluded from the term foreign DNA because such viruses can reversibly integrate into the chromosome of the recipient and/or kill the recipient. Transposable elements are excluded from the term foreign DNA because they can cause genetic rearrangement such as inserting replicas at other sites in the recipient, excising themselves from the chromosome causing inversion or deletion mutations. Transposable elements and viral DNA that can infect or transfect the recipients are unstable and, therefore, unsuited to the construction of a microorganism that contains at least one foreign DNA portion in the chromosome. This is particularly true when multiple foreign DNA portions are inserted.

The stably inserted foreign DNA of the present invention is actually incorporated into the chromosomal genome of the microorganism. Stably inserted foreign DNA refers to foreign DNA that is not involved in genetic rearrangement in the recipient microorganism or its progeny. The microorganisms of the present invention and their progeny are substantially free of genetic rearrangement involving the foreign DNA. By genetic rearrangement involving the foreign DNA is meant recombination between homologous portions of the recipient's chromosome leading to loss of foreign DNA, insertion of replicas of the foreign DNA in the genome of the recipient, or excision of the foreign DNA.

Foreign DNA that has been stably inserted in microorganisms of the present invention undergoes a functional change only as a result of mutagenic processes provoked by the repair or replication of DNA. The rate of such mutagenic processes can be defined by the rate at which auxotrophic mutations accumulate in a population or recipient organisms that has been transformed by the foreign DNA. For a discussion of auxotrophic mutations and methods for determining mutation rates, see J. Miller, *Experiments in Molecular Genetics* 121–82 (Cold Spring Harbor Laboratory 1972). A convenient test for the frequency of an auxotrophic mutation in a recipient is the frequency of chlorate-resistant mutations which can be measured as described in C. MacGregor et al. (1971) *J. Bacteriol.* 108: 564–570. The function of foreign DNA stably contained in the chromosome of a microorganism of the present invention is lost from the microorganism at a frequency that is not substantially greater than the highest frequency of a auxotrophic mutation in the organism. The frequency of mutagenesis is substantially lower than the frequency of recombination between homologous chromosomal DNA. After growing a culture for forty generations without selective pressure, for example, nearly 1,000 microorganisms of the present invention were tested for loss of function of the foreign DNA. All of the microorganisms tested exhibited the foreign DNA function. In contrast, when DNA was inserted into the chromosome in a manner that allowed recombination between homologous regions of the chromosome, at least 22% of the microorganisms tested had lost the inserted DNA function after forty generations in the absence of selective pressure. (See Example 2, infra.) Viral DNA or transposable elements that have the ability to integrate or provoke rearrangement in the recipient DNA are per se unstable and are excluded from the definition of foreign DNA as discussed above.

The microorganisms of the present invention are procaryotes (i.e., organisms within the kingdom Monera). Procaryotic organisms lack a nuclear envelope around their chromosome, such as is found in eucaryotic organisms. Procaryotic organisms are generally divided into the phyla schizophyta (all bacteria) and cyanophyta (blue-green algae or cyanobacteria). Typical examples of bacterial genera to which the present invention is applicable include, inter alia, Bacillus, Pseudomonas, Escherichia, Azotobacter, Rhizobium, Rhodopseudomonas, Streptococcus, Haemophilus and Klebsiella. Examples of cyanobacteria to which the present invention is directed include, inter alia, the genera Aphanocapsa, Anabaena, Nostoc, Oscillatoria, Synechococcus, Gloeocapsa, Agmenellum, Scytonema, Mastigocladus, Arthrosprira and Haplosiphon.

The preferred microorganisms of the present invention are cyanobacteria, which are gram-negative procaryotes. Cyanobacteria are photosynthetic unicellular organisms which are either free-living or in symbiotic association with bacteria, fungi, plants, or animals. They are found in lakes, rivers, oceans, mineral hot springs, soil (tropical to arctic) and on rocks and buildings.

Some are filamentous organisms and several species can fix nitrogen.

Cyanobacteria have the ability to synthesize chemicals from air, water and inorganic salts utilizing the energy of sunlight. In a particularly preferred embodiment of the present invention, therefore, photosynthetic cyanobacteria are contemplated whose chromosomal structure has been altered. Cyanobacteria can produce metabolites, such as carbohydrates, proteins, lipids and nucleic acids, from $CO_2$ (from the air), water, inorganic salts and light. With a nitrogen fixing cyanobacteria, nitrogen containing salts need not be added because the cyanobacteria can fix $N_2$ from the air. By introducing into a recipient cyanobacteria foreign DNA portions that encode new biochemical pathways, important and useful products can be produced photosynthetically. If the precursor of the foreign biochemical pathway is a metabolite of cyanobacteria, the product of the pathway can be produced solely from air, water, inorganic salts and sunlight. Additional precursor may be added, however, to increase the product yield. If the precursor is not a metabolite of the cyanobacteria, then precursor can be added to cultures of the cyanobacteria. In this case, it is preferred that the precursor be a readily available and inexpensive material such as a waste byproduct of other processes (e.g. lignosulfonates or casein).

Since the microorganisms of the present invention are readily produced by introducing a DNA insertion vehicle within the cell, preferably a circular vehicle comprised of a chimeric plasmid, a consideration in selecting a recipient organism is the ease with which it takes up exogenous DNA. Particularly preferred organisms in the present invention are those cyanobacteria which have been shown to have a naturally occurring system for the uptake exogenous DNA such as *Gloecapsa alpicola, Agmenellum quadruplicatum* and *Anacystis nidulans*. If a bacterium is employed, bacteria which spontaneously take up exogenous DNA, such as *Bacillus subtilis*, are preferred. The insertion vehicle employed in present invention, however, can also be introduced into procaryotes, such as *E. coli*, that take up exogenous DNA only through artificial manipulation. Methods for introducing exogenous DNA into other procaryotes are known in the art.

Figure 2:
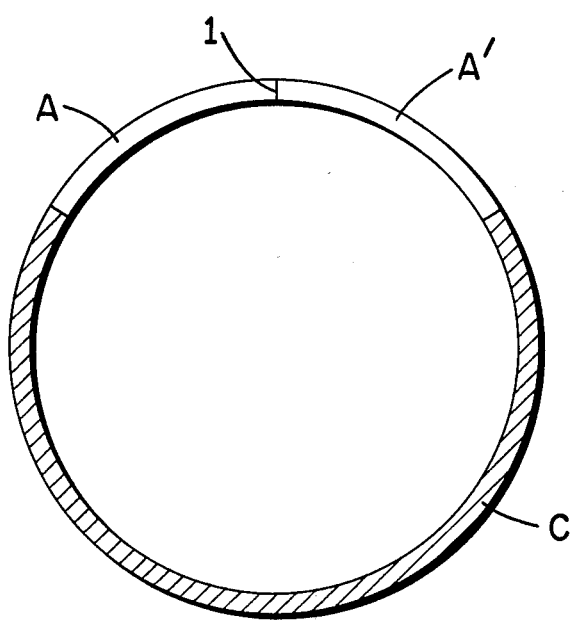
FIG. 2 is a schematic representation of the circular chimeric DNA molecule from which the vehicle of FIG. 1 is made.

Placement of the foreign DNA into the insertional DNA of the unloaded insertion vehicle may be accomplished using recombinant DNA technology. While the insertion vehicle can be either linear or circular, it is technically difficult to load a linear insertion vehicle with foreign DNA. Loading linear vehicles in vivo is not feasible because linear DNA cannot be maintained due to exonuclease activity in cells. Loading linear insertion vehicles in vitro can be accomplished but is inefficient because cleavage of the unloaded linear vehicle prior to insertion of the foreign DNA can result in shuffling the orientation of the insertional DNA fragments upon rejoining. From the standpoint of efficiency, these problems are obviated if circular vehicles, such as depicted in FIGS. 1 and 2, are employed. For efficient loading, the transformation vehicle desirably contains one or more unique restriction cleavage sites, or "loading sites," located in or near the central portion of the insertional DNA (i.e, sites in the insertional DNA for an endonuclease that cleaves at no other sites).

A "loaded" circular DNA insertion vehicle employed in the production of microorganisms of the present invention in its simplest form is comprised of three components as is shown in FIG. 1. The loaded insertion vehicle is made from an unloaded insertion vehicle or plasmid as depicted in FIG. 2. The structure of the unloaded vehicle is substantially the same as that of the loaded vehicle described in FIG. 1, excepting that there is no foreign DNA portion B and there is a restriction site 1 at the junction of insertional DNA portions A and A'.

Portions A and A' are termed insertional DNA. The insertional DNA is homologous to a stable region of DNA in a chromosome of the recipient organism. Portions A and A' are homologous to adjacent chromosomal DNA regions in the recipient and are ideally derived from a single fragment of chromosomal DNA from the recipient organism that has been cleaved at a centrally located restriction site (the loading site). "Adjacent" regions in the chromosomal DNA of the recipient means that either (1) chromosomal DNA regions that are immediately adjacent to each other, or (2) chromosomal DNA regions that are separated only by nonessential DNA. Portions A and A' are, relative to each other, in the same orientation in the insertion vehicle as are the homologues of A and A' in the chromosome of the recipient organism. In other words, the ends of the homologous regions in the chromosome closest to each other correspond to the end portions of A and A' in contact with DNA portion B in FIG. 1 (or restriction site 1 in FIG. 2).

The insertional DNA should have as long a length as practical on either side of the loading site. For example, foreign DNA portions were loaded randomly into insertional DNA segments having an average length between 80,000 and 120,000 base pairs in a linear insertion vehicle so that the great majority of foreign DNA was located thousands of base pairs from the ends of the insertion vehicles. There was a 400-fold increase in transformation efficiency (based on transformations per foreign DNA segment) with these linear insertion vehicles over an insertional DNA segment 4,100 base pairs long with a single loading site 500 base pairs from one end in a circular insertion vehicle. Insertional DNA should generally have at least 100 base pairs on either side of the loading site to obtain reasonable transformation efficiency. The length of the insertional DNA has not been found to affect the stability of the inserted foreign DNA.

Foreign DNA portion B, also referred to herein as interrupting DNA, is ligated between DNA portions A and A'. Useful foreign DNA which can be inserted into the chromosome of the recipient organism include genes which encode the production of proteins (e.g., an enzyme in a metabolic pathway) or regions that regulate gene expression (e.g., promoters and operators). Transformation efficiency has been found to drop as the length of the interrupting (foreign) DNA increases. For example, when the interrupting DNA is 1,300 base pairs long, there is a 7-fold increase in transformation efficiency over foreign DNA 4,000 base pairs long, all other conditions being equal. Although it is possible to insert quite long foreign DNA portions (e.g., up to at least 20,000 base pairs), it is desirable to use the shortest DNA length that will encode the desired information.

DNA segment C, or flanking DNA, is ligated to the opposite ends of DNA portions A and A'. Flanking DNA is so-called because it flanks and does not interrupt the insertional DNA. Flanking DNA is derived ideally from a plasmid compatible with and having the ability to replicate in a microorganism other than the recipient organism. The flanking DNA segment is required only in circular insertion vehicles. Since a linear vehicle only need be comprised of homologous DNA portions A and A' and interrupting DNA portion B.

When the flanking DNA is derived from a plasmid which is compatible with and replicates in a second microorganism, the flanking DNA is preferably derived from an entire plasmid which has been cleaved at a single restriction site. A functioning replcon in the flanking portion allows the transformation vehicle to be cloned in a microorganism other than the recipient organism in large quantities. No replicon in the insertion vehicle (including any replicon in the flanking DNA), however, should be functional in the recipient organism since it is the function of the insertion vehicle to transform the chromosome and not to replicate automonously in the recipient organism. It is also desirable to use a plasmid which contains a gene for a selectable phenotype (e.g., antibiotic resistance) to aid in the isolation of plasmids.

To stably insert the foreign gene or DNA portion contained in the interrupting DNA into the chromosomal genome of a recipient organism, the loaded transformation vehicle is introduced inside the cell membrane of the recipient. If the recipient organism naturally takes up exogenous DNA, the loaded transformation vehicle need only be introduced into a culture of the recipient organism. If the recipient organsim does not naturally take up exogenous DNA, the loaded plasmid can be introduced into the cell by conventional methods known in the art (e.g., conjugation or treatment with $CaCl_2$). See M. Suzuki & A. Szalay, (1979) *Meth. Enzymol.* 68: 331–341.

If the insertion vehicle is circular, the stably inserted transformant will usually have to be distinguished from two other types of unstable transformants. In one type of unstable transformant, the flanking DNA and the insertional DNA are added (i.e., an additive recombinant event) to the chromosome. If the flanking DNA expresses a selectable phenotype, this type of transformant is readily distinguished. In the second type of unstable transformant, the entire vehicle (interrupting, insertional and flanking DNA) is added to the chromosome. If both the interrupting (foreign) DNA and flanking DNA express selectable phenotypes, this type of transformant is also readily isolated. The instability of these types is believed to arise because there are two homologous regions in the chromosome; insertional DNA has been added to the chromosome rather than undergoing recombinant exchange. This would lead to loss of the interrupting DNA through recombination between the two homologous regions in the chromosome.

Pure cultures of the recipient organism with stably inserted foreign DNA can be obtained by selecting those organisms which have been stably transformed. Selection methods, well known in the art, include testing colonies grown from individual cells for product or other expressable phenotype, and colony hybridization. See M. Grunstein et al., (1975) *Proc. Natl. Acad. Sci USA* 72: 3962–3965. By pure culture is meant a culture of a species of microorganisms containing foreign DNA stably inserted into the chromosome that is substantially free of the same microorganism without foreign DNA in the chromosome.

Applicants have demonstrated that when a transformation vehicle according to the present invention is employed, foreign DNA can be stably inserted into the chromosomes. Once inside the cell membrane, the insertional DNA portions undergo recombination with the chromosome of the recipient organism at the site of homology between the insertional DNA and the chromosomal DNA. Since the foreign DNA is ligated between the adjacent portions of insertional DNA, the foreign DNA is carried into the chromosomal DNA of the recipient organism. Foreign DNA so inserted has been found to be a stable component of the chromosomal genome.

Applicants believe, but do not wish to be bound by their theory, that the actual insertion of foreign DNA into a chromosome takes advantage of a natural recombination event which occurs in a wide variety of both eucaryotic and procaryotic organisms. In fact, the method of the present invention should be generally applicable to eucaryotic organisms by introducing viable loaded insertion vehicles of the present invention inside the nuclear membrane of eucaryotes. The recombination event involves recombination between two molecules of DNA, identical in a portion of the molecules except for the presence in one of the molecules of a heterologous insertion. Recombination results in the transfer of the latter from the first DNA molecule to the second.

By stably inserting several foreign genes into the chromosomes of a microorganism, multistep biosynthetic pathways can be introduced which synthesize nonproteins. After identifying and isolating all the genes necessary in a desired biochemical pathway, the method of the present invention can be straightforwardly applied to produce a microorganism that will produce the desired product. Biological systems exist which produce chemicals of industrial importance, such as butanol, acetone, polysaccharides, carotenoids, hydrocarbons and molecular hydrogen. Genes for other biological systems can be isolated or synthesized. An in vivo method of producing such chemicals, particularly photosynthetically, is obviously of great value.

There are a multitude of applications for the present invention. For example, the genes for butanol-acetone fermentation (which produces butanol and acetone from glucose) are found in *Clostridium acetobutylicum.* See G. Gottschalk, *Bacterical Metabolism* 182 (Springer Verlag 1979). Stable introduction of those genes into a cyanobacterium provides a blue-green algae with a capability of producing butanol and acetone. All microorganisms produce glycerol. See, e.g., A. Newman, *Glycerol* (CRC Press 1968); L. Stryer, *Biochemistry* 292 (Freeman 1975). Glycerol production can be enhanced in a selected microorganism by introducing foreign DNA that affects the expression of the genes responsible for glycerol production. Production of hydrogen from water by a cyanobacteria is possible by mutating ferredoxin-NADP oxidoreductase, so that electrons produced by photosynthesis accumulate on ferrodxin, and by inserting a foreign gene encoding a hydrogenase into the mutated cyanobacteria. See, e.g., J. R. Benemann et al., (1982) *Proc. Natl. Acad. Sci. USA* 70: 2317–2320.

When several foreign genes are introduced into a recipient to, for example, introduce a new biochemical pathway, several transformation steps may be employed. In such cases where the foreign DNA inserted in one step encodes no selectable phenotype in the recipient organism, it is desirable to link the foreign DNA to a selectable gene to aid in the identification of stable transformants. A selectable gene can be spliced into the insertional DNA such that a unique loading site is located either within a nonessential region of the selectable marker, or at the molecular juncture between the selectable marker and one of the insertional DNA portions. In the latter case, the unloaded vehicle has the same configuration as in FIG. 2, except that an additional foreign gene that expresses a selectable phenotype is located between restriction site 1 and either DNA portion A or A'. Preferably, there is only one restriction site for the endonuclease of site 1 in the unloaded insertion vehicle.

In one preferred embodiment of the invention, insertion vehicles can be constructed by the following relatively simple procedure.

First, insertional DNA is isolated from the chromosome of the recipient organism by cleavage with a restriction enzyme. DNA fragments of the desired length, preferably 5000 to about 10,000 base pairs long, are isolated by electrophoresis. The desired fragments are cloned into a restriction site of a plasmid (which becomes the flanking DNA) from another microorganism (host organism). The plasmid from the host organism desirably expresses a selectable phenotype in the host and the recipient. The recombinant plasmids are used to transform the host organism and transformants are isolated according to phenotypes encoded on the plasmid. Milligram quantities of the mixture of recombinant plasmids are isolated from the host organism.

In the next step, it is necessary to isolate acceptable unloaded insertion vehicles from the mixed recombinant plasmids collected above. Acceptable insertion vehicles are those having centrally-located loading sites that are not within insertional DNA that is homologous to an essential gene in the recipient organism. One method of isolating acceptable insertion vehicles is to construct restriction cleavage maps of a number of the recombinant plasmids. This approach is unnecessarily laborious.

A simpler approach is to allow the recipient organism itself to isolate useful insertion vehicles. First, the mixture of recombinant plasmids is cleaved with a restriction enzyme that has sites only within the insertional DNA. The enzyme should not have restriction sites within the flanking DNA or at the junctions between the insertional DNA and the flanking DNA. Second, interrupting (foreign) DNA is ligated into the cleaved plamids. The interrupting DNA desirably contains a gene which expresses a selectable phenotype distinguishable from the selection marker in the flanking DNA.

The plasmids containing interrupting DNA are then used to transform a culture of recipient microorganisms. Isolated transformants which exhibit the selectable phenotype of only the interrupting DNA have obviously been transformed by a chimeric DNA molecule that is active as an insertion vehicle. The insertion vehicle itself, of course, is destroyed in the process of integration of the interrupting DNA into the recipient chromosome.

To reconstruct insertion vehicles, chromosomal DNA is isolated from several of the transformants. Cleaving the recovered chromosomal DNA from the transformants with the restriction enzyme originally used to isolate chromosomal DNA from the recipient organism (to be employed as insertional DNA) and then ligating the cleaved chromosomal DNA to cleaved plasmid DNA (flanking DNA) that contains a selection marker will yield a mixture that contains acceptable loaded transformation vehicles admixed with ligation products. By transforming the host microorganism and selecting for the phenotypes expressed by both the interrupting DNA and the flanking DNA, acceptable insertion vehicles which have a loading site in a nonessential region and which have been demonstrated to be effective can be isolated.

If it is desired to insert other foreign DNA into the reconstructed insertion vehicle, the loaded insertion vehicles can be unloaded by cleavage of the junctions between the insertional DNA and the interrupting DNA with the restriction enzyme described above which has restriction sites only within the insertional DNA. Alternatively, it may be desired to retain the foreign gene with its selection marker and load the insertion vehicle with nonselectable foreign DNA. In this case, it is preferred to eliminate from the insertion vehicle one of the restriction sites at the junctions between interrupting and insertional DNA portions. To do this, the insertion vehicle loaded with the selection marker (foreign DNA) is partially digested with the endonuclease active at the restriction sites on either side of the selection marker. Only enough enzyme is used to cleave about 30% of the vehicles at one site. The DNA is then purified and linear molecules the length of a circular vehicle that has been cleaved at only one point are isolated by electrophoresis. DNA polymerase is then employed to blunt the trailing ends ("sticky" ends) of the linear DNA molecules. This procedure destroys the restriction site. DNA molecules with the blunted ends are then ligated in a solution which has a very low concentration of DNA and a very high concentration of T4 DNA ligase to join linear molecules into a circular form. This mixture is then used to transform a host microorganism and several transformants are chosen for further examination. Transformants containing acceptable insertion vehicles (i.e, an insertion vehicle with a selection marker between a insertional DNA portion and a single loading site) are identified by isolating plasmid DNA, digesting it with restriction enzymes, and subjecting the linear digestion products to electrophoresis to identify vehicles that have been cleaved at a single site.

The following examples are included for illustrative purposes only and are not intended to limit the scope of this invention.

EXAMPLE 1

The following example describes the construction of a loaded transformation vehicle suitable for the transformation of *A. nidulans*. An *A. nidulans* strain (*A. nidulans* R-2 isolated by S. V. Shestakov et al., (1970) *Molec. Gen. Genet.* 107: 372–375) containing a gene within the chromosome capable of complimenting the thi-1 mutation in *E. coli* was lysed and DNA was isolated by dye-bouyant density centrifugation. Plasmids pBR322 and pACYC184 were isolated by dye-bouyant density centrifugation of lysozyme-sarkosyl lysates of appropriate *E. coli* strains. Plasmid pBR322 is a self-replicating *E. coli* plasmid which contains a selection marker which encodes resistance to ampicillin and is employed as the flanking DNA. The replicons in pBR322 and pACYC184 are not functional in *A. nidulans*. Plasmid pACYC184, which encodes resistance to chloramphenicol, is employed as the foreign or interrupting DNA.

A mixture of broken plasmids and chronosomal DNA from *A. nidulans*, at a concentration of 50 micrograms of DNA per milliliter was digested with Sau3A restriction endonuclease under conditions specified by Bethesda Research Laboratories, Inc. (BRL). The enzyme concentration, 6 units per milliliter, was chosen to provide incomplete digestion after a 30 minute incubation at 37° C. To stop the reaction, 0.080 ml of 0.25M EDTA was added to the 2 ml reaction mixture. The partially digested DNA was fractionated by electrophoresis through a 0.7% agarose gel and DNA fragments 5000 base pairs and larger were recovered from the gel by electroelution as described by Yang et al, (1979) *Meth. Enzymol.* 68: 176–182.

The purified *A. nidulans* DNA fragments were ligated to pBR322 DNA cleaved beforehand with BamHl and treated with bacterial alkaline phosphatase. The 0.220 ml ligation mixture contained pBR322 DNA at a concentration of 15 ug/ml and *A. nidulans* DNA at 8.6 ug/ml. The ligation mixture was incubated at 14° C. for 12 hours under ligation conditions specified by Boehringer-Mannheim. The reaction was terminated by addition of 0.011 ml of 0.25M EDTA. The ligated DNA was used to transform *E. coli* HB101 according to the method of Bolivar and Backman, (1979) *Meth. Enzylmol.* 68: 245. A total of $5 \times 10^5$ independent transformants resistant to ampicillin were obtained. Greater than 99.9% of the transformants contained chimeric plasmids with insertions of *A. nidulans* DNA. A mixed culture of the transformants is designated as a "gene library" of *A. nidulans* DNA in *E. coli*.

*E. coli* HB101 which contains the gene library plasmids, has a thi1 mutation that blocks the biosynthesis of thiamine. By plating the gene library culture on medium lacking thiamine, a chimeric plasmid designated pKW1006 thi+ was identified.

Plasmid pKW1006 thi+ contained only cleavage site for BamHl located at one of the junctions between flanking DNA pBR322 and the cloned insertional DNA fragment from *A. nidulans*. To eliminate this cleavage site, the plasmid was digested exhaustively with BamHl and was used to transform *E. coli* HB101 to ampicillin resistance. From one of the transformants, a new plasmid, pKW1034 thi+, was recovered which was identical to pKW1006 thi+ except for a deletion of about 700 base pairs bracketing the BamHl cleavage site. The foreign interrupting DNA, pACYC184, had been cleaved with BamHl and, therefore, could only be inserted at a BamHl cleavage site in the insertional DNA. Since pKW1034 thi+ contained no BamHl cleavage sites in the insertional DNA, BamHl sites were created at various positions using BamHl linkers. Plasmid pKW1034 thi+ was cleaved with HaeIII (BRL) in a 5 ml reaction mixture containing 50 micrograms of the plasmid DNA, 0.38 units of HaeIII and other ingredients as specified by BRL. Incubation was at 37° C. for 60 minutes. The reaction was terminated by the addition of 0.300 ml of 0.25M EDTA. The reaction mixture was extracted once with phenol, the volume was reduced to about 0.5 ml by extraction with n-butanol and the DNA was dialyzed against TE (10 mM Tris-HCl pH 7.5, 0.1 mM EDTA). Only 8% of the plasmids were cleaved by HaeIII as determined by agarose gel electrophoresis. The partial digest, therefore, presumably consisted of a population of full length linear molecules having termini at various HaeIII cleavage sites. BamHl linkers (CGGATCCG; BioLogicals) were added to the HaeIII partial digest. The 0.36 ml reaction mixture contained 9 nM pKW1034 thi+ DNA, 220 nM BamHl linker, 100 units of T4 DNA ligase per milliliter (Boehringer-Mannheim) and other ingredients as specified by Boehringer-Mannheim for ligation. Incubation was carried out at 15° C. for 15 hours. The reaction was terminated by the addition of 0.040 ml of 0.25M EDTA, extracted once with phenol and the DNA was dialyzed against TE (described above). Eight micrograms of the dialyzed DNA was digested with BamHl (250 units per milliliter) in a volume of 0.200 ml under conditions specified by Boehringer-Mannheim. The reaction mixture was incubated at 37° C. for 4.5 hours, followed by 10 minutes at 65° C. Then 0.020 ml of 0.25M EDTA was added and the DNA was dialyzed against TE as described above.

To the dialyzed DNA that had been digested with BamHl (an unloaded insertion vehicle cleaved in the insertional DNA portion), pACYC184 was ligated. The pACYC184 DNA (foreign or interrupting DNA) had been cleaved beforehand with BamHl and treated with bacterial alkaline phosphatase. A 0.100 ml reaction mixture containing 2.7 micrograms of the pKW1034-derived insertion vehicle 0.35 micrograms of pACYC184 DNA and 2 units of T4 DNA ligase was incubated for 17 hours at 15° C. The DNA in the incubated mixture was used directly to transform *E. coli* HB101. A plasmid, designated pKW1039 thi− was recovered from the transformants resistant to both chloramphenicol and ampicillin. The pKW1039 thi− plasmid contained pACYC184 in the interrupting position and pBR322 in the flanking position. The plasmid was unable to compliment the *E. coli* thi-1 mutation, presumably because the complimenting function was destroyed by the insertion of pACYC184 into the insertional DNA derived from *A. nidulans* DNA.

While plasmid pKW1039 thi− is suitable for inserting pACYC184 plasmid fragment into *A. nidulans*, it may be desirable at times to insert only a portion of a foreign plasmid fragment. To demonstrate this, pACYC184 was digested exhaustively with HaeII and the cleavage products were fractioned by electrophoresis through a 1.4% agarose gel. The largest fragment, which was 1,270 base pairs long and contained the chloramphenicol resistance gene, was purified according to the method of M. Albring et al., (1982) *Anal. Biochem* (in press) which is described below.

A HaeII digest of pACYC184 DNA (150 ug of DNA) was fractionated by electrophoresis at 2 volts per cm for 15 hours through a 64 percent agarose gel (Low Melting Point agarose; BRL). The gel was stained with ethidium bromide, the gel portion (5 ml) containing the slowest-migrating band of DNA (1.3 kb) was excised, and the agarose containing the DNA was dissolved by stirring for 15 min in 20 ml of 50% urea (w/w) plus 5 g of urea crystals. All operations were performed at room temperature in siliconized glassware and centrifugations were at 2000× g for 5 min. After the agarose was dissolved, the DNA was extracted from the agarose by adding 16 ml of DHA solution (40 ml. of n-butanol; 0.8 ml of glacial acetic acid; 4.6 ml of 2,2′-diethyldihexylamine from Eastman Kodak). The mixture was stirred vigorously for 5 min. The emulsion was centrifuged, the butanol phase (top) containing the DNA was recovered and saved, and the aqueous phase was extracted again with 11 ml of DHA solution. The second butanol phase was pooled with the first to give a volume of ca 30 ml. To extract the DNA from the butanol, the pool butanol phases were extracted with 6 ml of 1.25M ammonium acetate for 5 min, the emulsion was centrifuged, the bottom aqueous phase was saved, and the upper phase was extracted again with 6 ml of 1.25M ammonium acetate. The aqueous phases were pooled and were concentrated to about 0.4 ml by repeated extraction with n-butanol. The 0.4 ml sample was dialyzed against TE (described above).

To prepare flush termini, 5 micrograms of the purified fragment was incubated in a reaction mixture (0.454 ml) containing 20 mM TrisHCl, 10 mM $MgCl_2$, 1 mM 2-mercaptoethanol, 10 micromolar each of dATP, dGTP, dCTP, dTTP, and 18 units of *E. coli* DNA polymerase I large fragment (New England Bio. Labs) at a pH of 7.5 and a temperature of 37° C. for 4 hours, followed by 1 hour at 15° C. The reaction volume was increased to 0.478 ml by the addition of 0.013 ml of 20 mM ATP, 0.0045 ml 1M dithiothreithol, 0.004 ml of 14 micromolar BamHl linkers, and 45 units of T4 DNA ligase. This mixture was incubated at 15° C. for 4 hours and terminated by the addition of 0.027 ml of 0.25M EDTA and heating to 65° C. and holding that temperature for 10 minutes. The reaction mixture containing DNA (0.505 ml) was mixed with 0.037 ml of water, 0.0056 ml of 1M $MgCl_2$, 0.012 ml of 1M Tris-HCl (pH 7.0), 0.012 ml of 5M NaCl, 0.0021 ml of 14.3M 2-mercaptoethanol, 0.006 ml of bovine serum albumin (20 mg per ml held at 75° C. for 30 minutes) and 120 units of BamHl. This mixture was incubated at 37° C. for 14 hours and terminated by the addition of 0.040 ml of 0.25M EDTA followed by holding the mixture at 65° C. for 10 minutes and dialyzing it against TE (described above). Among the reaction products are DNA fragments encoding resistance to chloramphenicol and having single-stranded termini complementary to cleavage sites recognized by BamHl.

Plasmid pKW1039 thi$^-$ at a concentration of 30 ug/ml was digested exhaustively with BamHl, diluted ten-fold and ligated with T4 DNA ligase to remove pACYC184 from the interrupting position. This ligated DNA was used to transform *E. coli* HB101 and one transformant resistant to ampicillin and sensitive to chloramphenicol was recovered. Plasmid DNA isolated from this transformant was designated pKW1048 thi$^-$. The plasmid pKW1048 thi$^-$ contains a single BamHl cleavage site at the interrupting position defined in the parental plasmid pKW1039 thi$^-$.

Plasmid pKW1048 thi$^-$ was cleaved with BamHl, extracted with phenol and dialyzed against TE (described above). The cleaved pKW1048 thi$^-$ plasmid (3.6 ug/ml) was ligated to the 1,270 base pair fragment of pACYC184 (1.6 ug/ml) in a volume of 0.200 ml. The ligated DNA was used to transform *E. coli* HB101 and from among the transformants, a new plasmid designated pKW1065 thi$^-$ was recovered that specified resistance to both ampicillin and chloramphenicol. Plasmid pKW1065 thi$^-$ contained pBR322 in the flanking position and a 1,270 base pair fragment encoding chloramphenicol resistance in the interrupting position. The new plasmid was unable to complement the *E. coli* thi-1 mutation.

A more simplified method of constructing the above loaded insertion vehicle for *A. nidulans* is as follows.

*A. nidulans* chromosomal DNA can be cleaved with BglII and fragments between 5,000 and 10,000 nucleotides long isolated by electrophoresis. These fragments can then be cloned into the BamHl site of the plasmid pBR322. A partial homology between the cleavage sites of BglII and BamHl makes it possible to ligate together DNA fragments produced by these endonucleases. The hybrid junctions are not cleaved by either of the endonucleases. The recombinant plasmid can then be used to transform a strain of *E. coli* to ampicillin resistance.

Milligram quantities of the plasmid DNA can then be isolated from a mixed culture of the transformed cells. Next, the mixed plasmids are screened for those having loading sites located in the insertional DNA using the recipient organism (*A. nidulans*) to screen. First, the mixture of recombinant plasmids would be cleaved with BamHl. This enzyme will only cleave within the insertional DNA. Plasmid pBR322 in the recombinant plasmid has no BamHl restriction sites; the junctions between the insertional and flanking DNA are not cleavable by BamHl. Next, the mixture of cleaved DNA can be ligated to the purified 1,270 nucleotide base air fragment that encodes chloramphenicol resistance. This fragment can be conveniently isolated by electrophoresis of a BamHl digest of the plasmid pKW1065 employed in Example 1. The mixture of DNA will contain loaded insertion vehicles. The entire mixture can then be used to transform a strain of *E. coli*. Transformants resistant to both ampicillin and chloramphenicol will contain various recombinant plasmids in which the 1,270 base pair fragment is linked to insertional DNA. A preparative quantity of the mixture of recombinant plasmids can then be isolated from the resistant *E. coli* cultures.

This entire mixture of plasmids can then be used to transform a culture of *A. nidulans*. Type I transformants, those resistant to chloramphenicol but sensitive to ampicillin, are then isolated. Chromosomal DNA can be recovered from several different transformants and cleaved with BglII. The cleaved DNA can then be ligated to pBR322 cleaved with BamHl. This ligated DNA can then be used to transform a culture of *E. coli*. Transformants resistant to both chloramphenicol and ampicillin will contain useful insertion vehicles.

EXAMPLE 2

This example describes the transformation of *A. nidulans* with plasmid pKW1065 thi$^-$ produced by the method of Example 1.

In the example below, cell concentrations were estimated spectroscopically. An absorbance of 0.25 at 730 nM corresponds to about $1 \times 10^8$ cells per milliliter as determined by microscopic examination.

An actively growing culture of *A. nidulans* at a density of $3 \times 10^8$ cells per milliliter was diluted to $2.5 \times 10^7$ cells per milliliter in 400 ml of fresh BG-11 medium prepared according to Rippka et al. (1979) *J. Gen. Microbiol.* 111: 1-61. The diluted culture, perfused with air at a rate of about 3 ml per minute, was incubated overnight at 37° C. under 1,800 lux of "warm white" fluorescent light plus 100 lux from a 60 watt tungsten bulb. To sterilize the air, it was passed through a solution of 1% $CuSO_4$, a filter of activated charcoal (Gelman) and two membrane filters with a 0.20 um pore size (Gelman). When the culture reached a density of $1.4 \times 10^8$ cells per milliliter, 140 ml of cells were harvested by centrifugation at $5,000 \times$ g for 15 minutes at room temperature. The cell pellet was suspended in 20 ml of fresh BG-11 medium at a concentration of $1 \times 10^9$ cells per milliliter.

To 1.2 ml of competent cells from the fresh suspension in a $10 \times 13$ mm clear glass test tube was added 0.12 ug of pKW1065 thi$^-$ (from Example 1) in 0.006 ml of TE (as described in Example 1). The transformation mixture was incubated at 37° C. for 10 hours under the lighting conditions described above. The test tube was agitated intermittently to present settling of the cells. Aliquots of the mixture were spread onto the surface of membrane filters (Nuclepore MembraFil filters, 0.45 um pore size, cut to 8 cm diameter) resting on solid BG-11 medium in plastic petri plates. The solid medium was prepared by mixing equal volume of autoclaved BG-11 liquid (2× concentrated) and autoclaved Difco Bacto Agar (3% in water). Membrane filters were first sterilized by autoclaving in water. The cells on the filters were incubated under the growth conditions described above for 20 hours and then the filters were transferred to solid medium containing either chloramphenicol (5 ug/ml) or ampicillin (0.2 ug/ml), or both. The plates were then incubated for 10 days and the numbers of each type of transformant were tabulated. It was found that the cells had a plating efficiency of about 40%.

Three types of transformants were found. Type I transformants were the most common type and were resistant to chloramphenicol only. Of the total cells in the transformation mixture, one cell in one thousand was a type I transformant. Out of each 266 transformants, however, 250 transformants were of type I, 15 were of type II and 1 was of type III. As determined by Southern hybridization analysis, E. Southern, (1975) *J. Mol. Biol.* 98: 503-517, type I transformants contain a stably inserted single copy of the interrupting (foreign) DNA segment which is integrated in the recipient chromosome at a site homologous to the position of interrupting DNA in pKW1065 thi−. After growth of type I transformants for 40 generations in the absence of chloramphenicol, 948 cells were tested for chloramphenicol resistance. All of the cells tested exhibited chloramphenicol resistance, indicating that the foreign gene had been retained. The Type I transformants exhibited a mutant colony morphology; they formed colonies of very small size. The mutant phenotype is related to the location of interrupting DNA in the recipient chromosome (i.e., destruction of the thi-1 complimenting function).

Type II and type III transformants were also observed. Type II transformants are those in which the flanking DNA has been inserted in the chromosome of the recipient organism. Type II transformants demonstrate a resistance to ampicillin, but are sensitive to chloramphenicol. Type III transformants are resistant to both chloramphenicol and ampicillin. A type III transformant arises by the addition to the chromosome of at least one copy of the loaded plasmid, including the foreign DNA, the flanking DNA and the insertional DNA.

After growth of type II transformants for 40 generations in the absence of ampicillin, 22% of the cells had lost the ampicillin resistant phenotype specified by the foreign DNA. A possible explanation for this loss could be that in type II transformants, both the insertional DNA and the flanking DNA are added to the chromosome. This would lead to two homologous areas in the chromosome (the insertional DNA and the chromosomal DNA to which it is homologous) which could lead to excision of the foreign DNA.

After growth of a type III transformant for 40 generations in the absence of antibiotics, it was estimated that approximately 35% lost resistance to one or both antibiotics. As in the case of type II transformants, the addition of the loaded plasmid results in multiple homologous regions in the chromosome which would lead to excision of the foreign DNA.

EXAMPLE 3

The following example demonstrates the transformation of *A. nidulans* with a linear insertion vehicle.

Plasmid pKW1065 thi− was cleaved with the restriction enzyme HindIII. The plasmid contained one HindIII site located within one portion of the insertional DNA and another site approximately 300 base pairs into the flanking DNA from the end of the other insertional DNA portion. The cleaved DNA was used to transform a culture of A. nidulans in substantially the same manner as in Example 1. A 3-fold decrease in the number of stable type I transformants was observed visa-vis transformations with uncleaved pKW1065 thi− as in Example 1. No type II or III transformants were observed.

Since modifications will be apparent to those skilled in the art, it is intended that the invention be limited only by the scope of the appended claims.

We claim:

1. A cyanobacterium containing at least one stable foreign DNA portion covalently bonded directly to two originally adjoining segments of its chromosomal DNA oriented in relation to each other in the same manner as said segments are in said cyanobacterium, wherein said cyanobacterium and its progeny are substantially free of genetic rearrangement involving said foreign DNA and wherein said foreign DNA portion is derived from a source other than the genus of said cyanobacterium and is other than a transposable element.

2. The cyanobacterium of claim 1 that is a cyanobacterium that takes up exogenous DNA.

3. The cyanobacterium of claim 1 that is selected from the group consisting of Gloeocapsa alpicola, Agmenellum quadruplicatum and *Anacystis nidulans*.

4. The cyanobacterium of claim 3 that is Anacystis nidulans.

5. A pure culture of the cyanobacterium of claim 1, 2 or 3.

6. A method for producing a cyanobacterium having at least one stable foreign DNA chromosomal portion that comprises:
   (a) providing a DNA insertion vehicle containing first and second DNA portions containing DNA homologous to adjoining portions of a chromosome in said cyanobacterium said homologous DNA in said first and second DNA portions oriented in relation to each other in the same manner as said homolgous chromosomal DNA portions are in said cyanobacterium and a third DNA portion containing DNA foreign to the genus of said cyanobacterium, said third DNA portion located between and covalently bonded to said first and second DNA portions and wherein said foreign DNA is other than a transposable element; and
   (b) introducing said DNA insertion vehicle inside the cell membrane of said cyanobacterium to effect incorporation of the genetic material of said foreign DNA into the chromosomal genome of said cyanobacterium.

7. The method of claim 6 wherein said insertion vehicle is circular and said insertion vehicle can not autonomously replicate in said cyanobacterium.

8. The method of claim 7 wherein said first, second and third DNA portions in said insertion vehicle are located in a first DNA segment and a second DNA segment containing DNA that is not homologous to said cyanobacterium is covalently bonded to the ends of said first DNA segment to form a circle.

9. The method of claim 8 wherein said second DNA segment in said circular vehicle contains a replicon functional in an organism other than said cyanobacterium.

10. The method of claim 9 wherein said cyanobacterium is selected from the group consisting of *Anacystis nidulans, Gloeocapsa alpicola* and *Agmenellum quadruplicatum*.

11. The method of claim 10 wherein said cyanobacterium is *Anacystis nidulans*.

12. The method of claim 8 wherein said replicon is functional in a bacterium.

13. The method of claim 12 wherein said cyanobacterium is *Anacystis nidulans* and said bacterium is *E. coli*.

14. A circular DNA insertion vehicle comprising:
   (a) a first DNA segment comprising first and second DNA portions containing DNA homologous to adjoining portions of a chromosome in a cyanobacterium, said first and second DNA portions oriented in relation to each other in the same manner as said homologous chromosomal DNA portions are in said cyanobacterium and a third DNA portion containing DNA foreign to the genus of cyanobacterium said located between and covalently bonded to said first and second DNA portions, said third DNA portion encoding a selectable phenotype, said third DNA portion having a single restriction site for a particular restriction enzyme at a location nonessential to said expressible phenotype and wherein said foreign DNA is other than a transposable element; and
   (b) a second DNA segment containing a DNA portion that is not homologous to the chromosomal DNA in said cyanobacterium.

15. The insertion vehicle of claim 14 wherein said second DNA segment contains replicons which are functional only in organisms other than said cyanobacterium.

16. The insertion vehicle of claim 15 wherein said first and second DNA portions in said first DNA segment are derived from a single piece of chromosomal DNA.

17. The insertion vehicle of claim 14 wherein said cyanobacterium is selected from the group consisting of *Anacystis nidulans, Gloeocapsa alpicola,* and *Agmenellum quadruplicatum*.

18. The insertion vehicle of claim 15 wherein said cyanobacterium is *Anacystis nidulans*.

19. The insertion vehicle of the claim 17 wherein said cyanobacterium is *Anacystis nidulans* and said bacterium is *E. coli*.

20. The insertion vehicle of claim 15 or 16 wherein said replicon is functional in a bacterium.

* * * * *